United States Patent [19]
Minchin et al.

[11] Patent Number: 5,321,047
[45] Date of Patent: Jun. 14, 1994

[54] METHOD AND AMINES USED THEREIN

[75] Inventors: Michael C. W. Minchin, Oxford; John F. White, Wokingham, both of England

[73] Assignee: John Wyeth & Brother, Limited, Maidenhead, United Kingdom

[21] Appl. No.: 849,902

[22] Filed: Mar. 12, 1992

Related U.S. Application Data

[63] Continuation of Ser. No. 534,401, Jun. 7, 1990, abandoned.

[30] Foreign Application Priority Data

Jun. 3, 1988 [GB] United Kingdom ............. 8813185-9

[51] Int. Cl.$^5$ ................ A61K 31/165; A61K 31/195; C07C 237/20; C07C 229/14
[52] U.S. Cl. ................................ 514/567; 564/164; 564/165; 514/620; 514/564; 514/522; 562/443; 558/414
[58] Field of Search ............... 562/443; 564/164, 165; 514/567, 619, 567, 552; 558/414

[56] References Cited

U.S. PATENT DOCUMENTS

| | | | |
|---|---|---|---|
| 2,917,514 | 12/1959 | Anatol et al. | 564/164 |
| 3,419,525 | 12/1968 | Aolony | 562/443 |
| 3,712,924 | 1/1973 | Kruger et al. | 564/164 |
| 4,376,215 | 3/1983 | Deller et al. | 558/198 |
| 4,400,394 | 8/1983 | Kaplan et al. | 562/443 |

FOREIGN PATENT DOCUMENTS 2856753  7/1979  Fed. Rep. of Germany ...... 564/164

OTHER PUBLICATIONS

Szabo, L. et al., Bull. Soc. Chem. Belg., 86 (1-2), 35-8 (1977) (French).
British Journal of Pharmacology, 92, 5-11 and 13-18 (1987).
British Journal of Pharmacology, 76, 291-298 (1982).
L. E. R. S., vol. 4, pp. 119-126 (1986).
Journal of Pharm. and Exp. Therapeutics, 241, 251-257 (1987).
Molec. Pharm., 19, 27-30 (1981).
Trends in Neuroscience, 11, 13-17 (1988).
J. Chem. Soc., 2371-2376, 1955.
Chemical Abstracts 106, 78248 (1987).
Chemical Abstracts 97, 163499m (1982).
Afsah et al Chemical Abs. vol. 102 1985 Abstract 6101e.
Vinokurova et al Chemical Abstracts vol. 69 1968 Abstract 86494y.
Deller Chemical Abstracts vol. 97, 1982 Abstract 163499m.

*Primary Examiner*—Mukund J. Shah
*Assistant Examiner*—P. K. Sripada
*Attorney, Agent, or Firm*—Arthur G. Seifert

[57] ABSTRACT

The invention concerns a method for treating depression or senile dementia using a compound which acts selectively as an agohist of gamma aminobutyric acid (GABA) at GABA autoreceptors with the proviso that the compound is not fengabine and progabide.

21 Claims, No Drawings

METHOD AND AMINES USED THEREIN

This is a continuation of application Ser. No. 07/534,401 filed Jun. 7, 1990.

This invention relates to use of a new pharmacological activity and to certain amines possessing said pharmacological activity, to processes for preparing them and to pharmaceutical compositions containing them. More particularly this invention relates to the treatment of depression.

In the UK the annual referral rate for depression is around 300–400 per $10^5$ population of whom 10–15%. require hospitalisation. At present the most effective and safe treatment for severe depression involves electroconvulsive therapy (ECT) where the patient receives a series of controlled electric shocks. However such treatment understandably engenders an atavistic fear and apprehension in many patients. It also has undesirable side-effects, notably disturbance of memory.

ECT is also expensive and time-consuming to administer, requiring the presence of specialist doctors such as psychiatrists and anaesthetists. As an alternative to ECT, drug therapy provides a more acceptable treatment for the patient but at the present time such therapy has not displaced ECT as the optimal treatment in severe cases because it is not always effective. There is therefore a need for new drugs for the treatment of depression, especially drugs having new modes of action mimicking ECT.

The mode of action of ECT remains unknown but in recent years much has been learnt about the biological effects of electroconvulsive shock (ECS) in animals. In particular, repeated ECS, given in ways closely mimicking those used to administer ECT clinically, elicits in rodents changes in monoamine functions. These include: increased 5-HT-mediated behaviour, increased dopaminergic behaviour and depressed beta-adrenoceptor binding and sensitivity of the coupled adenylate cyclase. The last is also seen following chronic treatment with a number of antidepressant drugs.

The effects of repeated ECS are presumably a response or adaptation to the acute effects of the seizures. Among these acute effects are a marked change in the release, synthesis and level of gamma aminobutyric acid (GABA) in the brain. - see Green A. R. et al, British J. Pharmacol., 92, 5-11 and 13-18 (1987) and Bowdler et al, ibid, 76, 291-298 (1982).

GABA is one of the most widespread and abundant transmitters in the mammalian central nervous system and plays a major role in the control of brain ! excitability. It is similarly implicated in the benzodiazepine-mediated relief of anxiety. Recently, evidence has come to light which suggests that GABA transmission may also be involved in the therapeutic effects of some antidepressant treatments. In particular, new compounds designed as GABA agonists (eg. fengabine and progabide) have been shown in preliminary clinical trials to have antidepressant activity (vide infra). Taken together, these findings suggest that interventions directed specifically at GABA transmission may provide the basis of novel therapies for the treatment of affectlye disorders.

At present three GABA receptors have been identified in the central nervous system. These are (1) a $GABA_A$—receptor known to be mainly postsynaptic and mediating inhibition of neuronal firing - see for example Stephenson, F. A. Biochem, J., 249 pp 21-32 (1988); (2) a $GABA_B$ receptor located presynaptically and mediating the inhibition of release of a number of neuro-transmitters, eg. noradrenaline and aspartic acid, but not GABA - see for example Bowery, N. G. et al, Nature, 283, 92–94 (1980); and (3) a GABA autoreceptor which modulates the release of GABA from neurones - see for example Mitchell, P. R., and Martin, I. L. Nature, 274 904–905 (1978).; Arbilla, S. Kanal, J. L and Langer, S. Z. Eur. J.Pharmac., 57, 211–217 (1979) and Brennan M. J. W. et al, Molec. Pharmac., 19, 27–30 ( 1981 ).

The pharmacological importance of these receptors is currently a subject of investigation with a major part of the work involving the search for anticonvulsant drugs with a mode of action involving $GABA_A$ receptors. Two drugs acting on GABA receptors, progabide and fengabine, have also been shown to possess antidepressant effects in preliminary clinical trials -see P. L. Morselli et al, L.E.R.S. Vol 4 (1986) pp 119–126 and B.Scatton et al, Journal of Pharm. and Exp. Therapeutics., 241, 251–257 (1987). The latter workers showed that fengabine possessed a biochemical mode of action different from that of conventional antidepressants but that the mechanism whereby fengabine exerted its antidepressant actions was not yet clear. It was thought to derive from a GABAergic action, most likely at $GABA_A$ receptors.

In the case of progabide, Morselli et al also attributed the antidepressant effect to an increased GABAergic transmission.

We provide evidence herein that the antidepressant effect of progabide and fengabine is in fact due to their agohist action at the GABA autoreceptor.

The GABA autoreceptor is capable of regulating the release of GABA from GABAergic neurons which means an agohist at the autoreceptor would decrease the GABA release hence decreasing GABA function ie. an action opposite to that of $GABA_A$ agonists.

As far as we are aware it has not been suggested even remotely that the GABA autoreceptor is linked to an antidepressant effect. Previously the autoreceptor was believed to have the same pharmacology as the $GABA_A$ site - see Molec. Pharm, 19, 27-30 (1981). We have now surprisingly found that the GABA autoreceptor has its own distinct pharmacology and that there are compounds having selective agohist activity at the GABA autoreceptor. These compounds have valuable medical uses.

Accordingly in one aspect this invention provides a compound for use in. treating depression characterised in that the compound has selective agohist activity at GABA autoreceptors and a pharmaceutical composition comprising such a compound.

This invention also provides a method for treating depression in humans which comprises administering an effective amount of a compound which possesses selective agonist activity at GABA autoreceptors.

This invention also provides a pharmaceutical composition for treating depression which comprises a compound possessing selective GABA autoreceptor agonist activity and a pharmaceutical acceptable carrier.

There is evidence that compounds acting at the benzodiazepine receptor as inverse agonists decrease GABA function in the brain and thus increase acetylcholine transmission. In addition, probably as a consequence of these actions, they facilitate memory in animals and man (see Sarter. M. et al. Trends in Neuroscience, 11 13–17, 1988). Compounds acting selectively as GABA autoreceptor agonists would be expected to have similar actions.

Accordingly, another aspect of this invention provides a compound having selective agonist activity at GABA autoreceptors for use in the preparation of a medicament for treating senile dementia and other forms of memory impairment. This invention also provides a method of treating senile dementia and other forms of memory impairment in mammals which comprises administering an effective amount of a compound which possesses selective agonist activity at GABA autoreceptors.

In this invention it is preferred that the compound having GABA autoreceptor agonist activity is selective in that it has little or no activity at $GABA_A$ receptors. This is because $GABA_A$ agonist activity would tend to counteract the effect of the autoreceptor agonist. $GABA_A$ antagonist activity tends to cause convulsions. For example the selectivity for the GABA autoreceptor relative to the $GABA_A$ receptor is preferably greater than 100, most preferably greater than 1000.

We have found that one general class of compounds in which selective GABA autoreceptor agonist activity can be observed is tri-substituted amines in which one of the substituents is a 3- or 4-alkanoic acid which itself may be substituted and derivatives thereof, such as an amide or substituted amide. Within such a general class the observation of GABA autoreceptor activity depends on the nature of the substituents.

In a further aspect of this invention there are provided compounds having a tri-substituted amine structure with one substituent being a 3- or 4- carbon alkyl group carrying a carboxylic acid or amide function possessing selective GABA autoreceptor agonist activity. More particularly this invention relates to e mono- and di-(arylalkyl)amine derivatives and related compounds possessing pharmacological activity, and intermediates of closely related structure.

Certain di-(arylalkyl)amine derivatives are known in the literature. The reaction of dibenzylamine with 3-chloropropyl cyanide to give 3-dibenzylaminopropyl cyanide and subsequent hydrolysis of the cyanide to give 4-dibenzylaminobutyric acid hydrochloride is described by M E Gittos and W Wilson in Journal of the Chemical Society, (1955) 2371–2376. The latter compound is also described in Chemical Abstracts 106, 78248(1987) where it is used to prepare derivatives of daunorubicin. 4-Dibenzylaminobutyramide and 4-dibenzylaminopropyl cyanide are disclosed in Chemical Abstracts 97, 163499m as intermediates in the preparation of 4-aminobutyric acid amide hydrochloride. Various -dibenzylaminoalkyl cyanides and related compounds are disclosed in J. Med. Chem., 1975 18(3) 278–284 as starting materials for fibrin stabilizing factor inhibitors.

Accordingly this invention provides a compound for use as a pharmaceutical having formula:

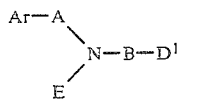

(Ia)

or a salt thereof, wherein E represents lower alkyl or a group $Ar^1—A^1—$; $Ar^1$ are the same or different aryl groups (including heteroaryl) which are optionally substituted, eg. by one or more substituents commonly used in pharmaceutical chemistry such as lower alkyl, lower alkoxy, halogen haloloweralkyl, haloloweralkoxy, cyano, amino (including substituted amino eg. mono- or di-loweralkyl amino) and nitro;

A and $A^1$ are the same or different alkylene groups having one or two carbon atoms linking Ar or $Ar^1$ to N and optionally substituted by lower alkyl and/or optionally substituted aryl, B is an alkylene group of 3 or 4 carbon atoms, which may be substituted by lower alkyl;

$D^1$ represents $CONR^1R^2$ or COOH where $R^1$ $R^2$ are independently hydrogen, lower alkyl or aralkyl of 7 to 12 carbon atoms.

The compounds of formula Ia can be prepared from intermediates of formula Ib

(Ib)

wherein Ar, A, E and B are as defined above and D represents CN, COhal, $CH_2OH$, CHO or an ester function COOR.

By the term "lower" is meant a group containing 1 to 6 carbon atoms.

Examples of Ar and $Ar^1$ are mono- or bi-cyclic aryl groups such as carbocyclic aryl groups of 6 to 10 carbon atoms (eg. phenyl or naphthyl) and heteroaryl groups of 5 to 10 ring atoms in which the heteroatom is selected from oxygen, nitrogen and sulphur (eg. pyridine, furan, thiophene) or aromatic groups containing two or more such heteroatoms (eg. thiazolyl). Bicyclic heteroaryl groups are exemplified by quinoline and benzofuran.

Examples of A and $A^1$ are independently —($CH_2)_m$—optionally substituted by lower alkyl and/or aryl where m is 1 or 2. Preferably A and $A^1$ are independently —$CHR^3$—where $R^3$ is hydrogen, lower alkyl, eg. methyl or ethyl, or optionally substituted aryl as defined for Art, eg. phenyl. Examples of B are —$CH_2CH_2CH_2$— and —$CH_2CH_2CH_2CH_2$—which groups may be substituted by lower alkyl such as methyl, eg. B represents —$CH(CH_3)CH_2CH_2$— or —$CH_2CH(CH_3)CH_2$.

Examples of $R^1$ and/or $R^2$ are hydrogen, methyl, ethyl, propyl and benzyl.

Some compounds of formula Ib are known compounds. Accordingly in a further aspect this invention provides a compound of formula I (including compounds of formula Ia).

(I)

wherein E, Ar, $Ar^1$, A, $A^1$ and B are as defined above and D is COOH or $CONR^1R^2$ wherein $R^1$ and $R^2$ are as defined above or D is CN, COhal, $CH_2OH$, CHO or COOR where COOR represents an ester function (eg. R=optionally substituted alkyl, or alkyl or aryl) providing that (i) neither Ar-A or E is unsubstituted benzyl and (ii) when B is —$(CH_2)_4$— and D is CN then E is other than methyl, ethyl or p-chlorobenzyl.

Compounds of formula I wherein D is CN, COhal, $CH_2OH$, CHO or COOR where R is as defined above are useful as intermediates to compounds of formula I wherein D is COOH or $CONR^1R^2$.

The compounds of formula Ia as defined above possess pharmacological activity especially activity affecting the nervous system. In particular the compounds of formula Ia are inhibitors of gamma aminobutyric acid (GABA) release from nerve terminals via action on the GABA autoreceptor.

A number of compounds have previously been shown to be agonists at the GABA autoreceptor, for example muscimol, isoguvacine and THiP (see Merck Index 1983 No. 9214) but such compounds are non-selective in that they are also active at other GABA receptors (ie. $GABA_A$ and/or $GABA_B$). As far as we are aware no medical use has been attributed to the above-mentioned compounds based on their GABA autoreceptor activity.

Compounds showing selective properties at the GABA autoreceptor are desirable since additional activity at the other GABA receptors would cause many side effects such as sedation and adverse muscle tone actions.

The compounds of formula Ia demonstrate activity at GABA autoreceptors, more specifically they demonstrate agohist activity as shown by standard in vitro test procedures. Advantageously compounds of formula Ia appear to be selective in that they display little or no activity at $GABA_A$ or $GABA_B$ receptors. The following test procedures were used to measure activity at (a) GABA autoreceptors and $GABA_B$ receptors by inhibition of potassium-evoked GABA and noradrenalin release from rat cortex in vitro (Procedure 1); and (b) $GABA_A$ receptors by enhancement of [3H]-flunitrazepam binding in rat cortex in vitro (Procedure 2):

Procedure

Slices (0.25×0.25×2.0 mm) of rat cerebral cortex are prepared using a McIlwain tissue chopper. The slices are incubated in Krebs-Henseleit solution containing [$^3$H]-GABA ($10^{-7}$M) and [$^{14}$C]-noradrenaline ($10^{-7}$M) in the presence of amino-oxyacetic acid (AOAA) ($10^{-5}$M), pargyline ($10^{-6}$M) and ascorbic acid ($10^{-4}$M), for 20 minutes at 37° C., rinsed with 5 ml aliquots of Krebs-Henseleit solution and transferred to 10 superfusion chambers (volume 300 μl ). The slices are continuously superfused with Krebs-Henseleit solution (0.4 ml min$^{-1}$) containing AOAA ($10^{-5}$M) and fractions of -1 the superfusate collected every 4 minutes. Transmitter release is induced by 4 minute exposure to a Krebs-Henseleit solution containing 25 mM potassium (with concomitant reduction in sodium to maintain osmolarity) after 68 ($S_1$) and 92 ($S_2$) minutes of superfusion. The compound under study is added to the superfusing medium 20 minutes prior to the second potassium stimulation. The residual radioactivity in the slices at the end of the experiment together with that in the superfusate fractions is measured by liquid scintillation counting using a dual label programme for tritium and carbon-14.

Calculations: The amount of radioactivity [either tritium or carbon-14) in each fraction is expressed as a percentage of the respective total radioactivity in the tissue at the start of the respective collection period. The amount of radioactivity released above basal by the increased potassium is calculated and the ratio S2/S1 obtained. The S2/S1 ratio from drug-treated slices is expressed as a percentage of the control S2/S1 ratio. For compounds achieving inhibition of 30% or more $pD_2$ values are calculated from plots of inhibition of release versus concentration of drug. Failure to inhibit the release of noradrenaline indicates that the molecule has no $GABA_B$ agonist activity.

Procedure (2)

Cortices from six or more rats are excised and homogenised in 50 volumes (volume/weight) 50 mM Tris buffer (pH 7.4 at 37° C.) using a Polytron homogeniser on speed 5 for 30 seconds. Tissue is kept at 0° C. throughout the procedure. The homogenate is centrifuged at 40,000×g for 15 minutes and the pellet resuspended (Polytron 5, 10 sec. ) in 50 volumes (original weight) of Tris buffer. Centrifugation and resuspension is repeated followed by incubation at 37° C. for 10 minutes. The homogenate is centrifuged (40,000×g, 15 min), resuspended in 10 volumes (original weight) Tris and stored below −20° C. for more than 24 hours.

On the day of the experiment, membranes are thawed at 37° C. and made up to 20 volumes (original weight) with Tris Krebs (20 mM, see below). The membranes are homogenised (Polytron 5, 30 sec), incubated at 37° C. for 15 minutes and centrifuged at 20,000×x g for 10 minutes. This wash and resuspension is repeated two more times with the final pellet resuspended in 100 volumes (original weight) Tris Krebs ready for use.

The test compound (50 μl ) and 20 nM (final concentration) [$^3$H]-flunitrazepam (50 μl ) are dispensed in triplicate. The reaction is started by the addition of 900 μl of membrane preparation. After a 30 minute incubation at 37° C. the reaction is stopped by filtration through Whatman GF/B filters under reduced pressure using a Brandell Cell Harvester, with two 7.5 ml filter washings. The radioactivity retained on the filters is measured by liquid scintillation counting.

Tris Krebs composition: NaCl—136 mM, KCl-5 mM, $MgSO_4$—2 mM, $KH_2PO_4$—2 mM, $CaCl_2$—2 mM, Tris buffer (pH 7.4 at 37° C.)-20 mM, ascorbic acid-1 mM, disodium ethylenediamine tetraacetic acid-1 mM.

Calculations: Result are calculated as follows:

$$\frac{\text{dpm sample (enhanced binding)}}{\text{dpm control (non-enhanced binding)}} \times 100 = \% \text{ control}$$

RESULTS

In the aforementioned tests the following representative compounds gave the results shown:

| Compound | GABA autoreceptor pD2 values | Inhibition of release of noradrenaline at $10^{-5}$M | Enhancement of [3H]-flunitrazepam binding |
|---|---|---|---|
| 4-[N,N-Bis-(4-Chlorobenzyl)-amino]butyric acid | 7.0 | 0 | 0 |
| 4-[N,N-Bis-(4-Chlorobenzyl)-amino]butyramide | 6.6 | 0 | 0 |
| 4-(N,N-Dibenzylamino)butyramide | 7.0 | >20% | 0 |
| 4-(N,N-Dibenzylamino)butyric acid | 7.1 | 20% | 0 |
| 4-[N,N-Bis-(4-Methylbenzyl)-amino]butyric acid | 7.4 | 10% | 0 |
| 4-[N,N-Bis-(3,4-dichlorobenzyl-amino]butyric acid | 7.5 | 0 | 0 |

| Compound | GABA autoreceptor pD2 values | Inhibition of release of noradrenaline at $10^{-5}$M | Enhancement of [3H]-flunitrazepam binding |
|---|---|---|---|
| 4-[N,N-Bis-(4-methoxybenzyl)-amino]butyramide | 6.0 | 0 | 0 |
| 4-[N-(p-chlorobenzyl)-N-methyl]aminobutyramide | 7.5 | 0 | 0 |

In the aforementioned tests fengabine was found to have a pD2 value of 8.0 at the $GABA_B$ sites in vitro. We attribute the antidepressant activity observed for fengabine to its potent selective GABA autoreceptor activity. Progabide was also active at the GABA autoreceptor. We make no claim to the use of fengabine or progabide in the preparation of a medicament for use as an antidepressant.

The compounds were also tested for their effect on a GABA synapse in vivo in the following procedure:

Procedure 3

Experiments were performed on male albino rats (240-280 g) lightly anaesthetized with urethane (1.2-1.4 g/kg i.p.) or Halothane (0.7-1.0% in $O_2$). The animal's temperature was maintained between 36°-38° C. via a thermostatically controlled heating blanket.

The caudate nucleus and substantia nigra were approached dorsally after exposing the overlying cortex. Pulsations of the brain and cerebral oedema were minimised by allowing cerebral spinal fluid to leak from a cisternal puncture. The exposed cortex was bathed in warm liquid paraffin throughout the experiment. A coaxial bipolar stimulating electrode (tip separation 0.25 mm) was positioned stereotaxically in the caudate nucleus such that the tip of the electrode corresponded to the area delineated by the co-ordinates L 2.5; A 8.5-95; D 5. (Paxinos and Watson, 1986 ). Square wave pulses ( 50-300 μA 0.1-0.2 msec duration) were delivered at 0.5-1.0 Hz via the stimdlating electrode to evoke inhibitory, GABA-mediated synaptic responses in nigral neurones.

Extracellular recordings were obtained from single neurones in the ipsilateral substantia nigra via either the centre barrel ( 3.5M NaCl) of a multibarrelled microelectrode or a single barrelled electrode (3.5M NaCl), attached to but protruding 10-20 μ beyond, a multibarrelled electrode. The electrodes were lowered into the substantia nigra via a remote controlled stepping micromanipulator such that the electrode tip corresponded to the stereotaxic co-ordinates L1.5-2.5; A 3.0-4.0; D 7.0-8.5 (Paxinos and Watson, 1986). Unit firing was amplified, continuously monitored on an oscilloscope, electronically counted and displayed by a chart recorder and fed into a computor for the generation of peristimulus time histograms (PSTH) of synaptic responses. Each outer barrel of the multibarrelled electrode was filled with aqueous solutions of the following which were administered in the vicinity of the recorded neurones using standard microiontophoretic techniques: Compound of Example 5 (0.1M or 0.01M in 0.9% NaCl, pH 5.5), GABA (0.2M, pH 3.5), glycine (0.2M, pH 3.5), di-homocysteate (DLH) (0.2M, pH 7.2), N-methyl-D-Aspartate (NMDA) (0.05M in 0.165M NaCl, pH 7.0), quisqualate (0.02M in 0.165M NaCl, pH 7.0), kainate (0.2M in 0.165M NaCl, pH 7.0) and bicuculline methochloride (BMC) (0.005M in 0.165M NaCl, pH 5.0). Effects of agonist drugs on the GABA autoreceptor could be measured as an attenuation of the synaptic inhibition evoked by stimulation of the caudate. $GABA_A$ receptor agonism could be tested by ejecting drug directly onto the nigral meurone in the absence of synaptic inhibition.

The location of the recording and stimulating electrodes in the brain were verified after each experiment by histological examination.

Reference Paxinos G & Watson C (1986) The rat brain in stereotaxic coordinates. Academic Press.

Result

In this test the compound of Example 5 almost abolished synaptically-evoked, GABA-mediated inhibition in the substantia nigra without affecting postsynaptic $GABA_A$ receptors, when it was ejected iontophoretically in the vicinity of nigral neurones. This action of the compound of Example 5 was reversible and is entirely consistent with a selective agonist action at the GABA autoreceptor.

In another aspect this invention provides a compound of formula Ia for use as a pharmaceutical.

This invention also provides processes for preparing the compounds of the invention, including processes for preparing the pharmacologically active compounds of formula Ia via intermediates of formula I wherein D is CN, COOR, CHO, $CH_2OH$ or COhal.

Compounds of formula I may be prepared by any one of the following processes:

a) reacting a compound of formula II

wherein Ar, E and A are as defined above with a compound of formula III:

wherein B is as defined above and hal represents chlorine or bromine, to give a compound of formula I wherein D is CN,
or b) carrying out a reductive alkylation of a compound of formula II as defined above using a compound of formula IV

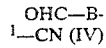

wherein $B^1$ is an alkylene chain of 2 or 3 carbon atoms optionally substituted by lower alkyl, in the presence of a reducing agent such as sodium cyanoborohydride to give a corresponding compound of formula I wherein D is CN and B represents $—CH_2—B^1—$;
or (c) reducing a compound of formula (V)

wherein $R^4$ is alkyl of 1 to 5 carbon atoms or $Ar^1—A^2—$; Ar, $Ar^1$, A and B are as defined above, $D^3$ represents CN, COOR or COOH and $A^2$ represents a direct bond or alkylene of 1 carbon atom optionally substituted by lower alkyl and/or aryl to give a corresponding compound of formula I wherein D is CN, COOR or COOH and E is $R^4CH_2$ wherein $R^4$ is as defined above;

or (d) reducing a compound of formula (VI)

$$Ar-A-\underset{\underset{E}{|}}{N}-CO-B^1-D^2 \quad (VI)$$

wherein Ar, A and E are as defined above, $B^1$ is as defined in connection with formula IV and $D^2$ represents CN, COOR or CHO to give a corresponding compound of formula I wherein B is —$CH_2B^1$— and D is CN, COOR or CHO, or (e) partially hydrolysing a compound of formula I wherein D is CN to give a corresponding compound of formula I wherein D is $CONH_2$;

or (f) hydrolysing a compound of formula I wherein D is CN or $CONH_2$ to give a corresponding compound of formula I wherein D is COOH;

or (g) reacting a compound of formula I wherein D is COOR or COhal with ammonia or an amine of formula $HNR^1R^2$ to give a corresponding compound of formula I wherein D is —$CONR^1R^2$;

or (h) hydrolysing an ester of formula I wherein D is COOR to give a carboxylic acid of formula I wherein D is COOH;

or (i) oxidising an aldehyde of formula I wherein D is CHO to give an acid of formula I wherein D is COOH;

or (j) oxidising an alcohol of formula I wherein D is —$CH_2OH$ to give an aldehyde or an acid of formula I wherein D is CHO or COOH;

or (k) oxidising a compound of formula $$\begin{array}{c} Ar-A \\ \phantom{Ar-}\diagdown \\ \phantom{Ar-A\diagdown}N-B-D^3 \\ \phantom{Ar-}\diagup \\ E \end{array} \quad (VII)$$

wherein Ar, A, E and B are as defined above and $D^3$ is $COCH_3$—C≡CH or —CH=$CH_2$ to give a compound of formula I wherein D is COOH;

or (l) hydrolysing a compound of formula $$\begin{array}{c} Ar-A \phantom{xxxxx} T^1 \\ \phantom{Ar-}\diagdown \phantom{xxx} \diagup \\ \phantom{Ar-A\diagdown}N-B^1-CH \\ \phantom{Ar-}\diagup \phantom{xxx} \diagdown \\ E \phantom{xxxxxxx} T^2 \end{array} \quad (VIII)$$

wherein Ar, A and E are as defined above, $T^1$ and $T^2$ are each independently an ester function, a nitrile or an acyl group, and $B^1$ is an alkylene group of 2 or 3 carbon atoms optionally substituted by lower alkyl to give a corresponding compound of formula I wherein B is —$B^1$—$CH_2$— and D is COOH;

or (m) esterifying an acid or acid halide of formula I wherein D is —COOH or COhal to give an ester of formula I wherein D is —COOR;

or (n) halogenating an acid of formula I to give an acid halide of formula I wherein D is COhal;

or (o) reducing an acid of formula I wherein D is COOH to give an alcohol of formula I wherein D is $CH_2OH$, or (p) acidifying a compound of formula I to give an acid addition salt thereof or neutralising an acid addition salt to give the free base form.

With regard to process (a) the reaction may be conveniently carried out in the presence of an inert solvent and a base such as a tertiary amine (e.g. diisopropylethylamine) with heating if required. Examples of suitable inert solvents are dimethylformamide, acetonitrile and dimethylsulphoxide.

With regard to process (b) the reductive alkylation is conveniently carried out in an inert solvent, depending on the reducing agent, and without heating. When the reducing agent is sodium cyanoborohydride the solvent may be an aqueous alcohol such as aqueous ethanol. Catalytic hydrogenation may also be used, eg using Pd/C and an alcohol solvent, e.g. ethanol.

Process (c) and (d) may both be carried out using a suitable reducing agent not affecting the $D^1$ or $D^2$ group for example ionic hydrogenation see Kursanor et al, Synthesis 1974, Vol 9, 633-651. Other reducing agents may be used, e.g. diborane or Raney nickel.

With regard to process (e) the partial hydrolysis of the nitrile to give the amide may be carried out in conventional manner under acidic or basic conditions. Methods for carrying out the transformation are extensively described in the literature—see for example the textbook Buehler and Pearson, Survey of Organic Syntheses, Wiley Interscience, 1970 pages 903-904, and references cited therein. The preferred method is to carry out the hydrolysis using aqueous sodium hydroxide in the presence of hydrogen peroxide and a phase transfer catalyst.

Process (f) may also be carried out in conventional manner using either acid or basic conditions as described in the literature. By way of illustration reference is directed to the textbook Buehler and Pearson, ibid at pages 751-754.

Process (g) may also be carried out in conventional manner using ammonia or amine preferably in alcoholic solution. Again by way of illustration reference is drawn to the textbook Buehler and Pearson, ibid pps 899-902. Where an acid halide is used as starting material it is preferred to employ an acid salt thereof in order to minimise reaction of the starting material with itself.

The hydrolysis process (h) may be carried out under acidic or basic conditions in conventional manner e.g. refluxing in 10% alkali metal hydroxide followed by acidification.

Processes (i) and (j) may be conveniently carried out using conventional chemical oxidising agents, e.g. potassium dichromate, potassium permanganate and oxygen/platinum catalyst. These and other methods are given in standard textbooks, see for example Buehler and Pearson, ibid, pps 545-549 and 760-764. Where process (j) is used to provide an aidehyde, overoxidation to the acid can be avoided by selective oxidation methods as described on pages 546-8 of Buechler and Pearson.

With regard to process (k) oxidation of the compound of formula VII wherein $D^3$ is $COCH_3$ may be effected by treatment with halogen and alkali (ie. the well known haloform reaction) e.g. by adding a solution of sodium hypochlorite or hypobromite to the ketone in alcoholic solvent. Oxidation of the compound of the formula VII wherein $D^3$ is $CH=CH_2$ or $-C\equiv CH$ may be effected by using potassium permanganate potassium iodate or ozone.

Hydrolysis process (l) is conveniently carried out under acidic conditions e.g. refluxing in dilute sulphuric acid.

Esterification process (m) may be effected by conventional means involving reaction with an alcohol ROH, see for example Buehler and Pearson, ibid, pps 802–809. Conveniently the reaction of the acid may be carried out with the alcohol as solvent and in the presence of mineral acid (e.g. HCl). The acid halide is conveniently in the form of an acid salt prior to reaction with the alcohol and the reaction is preferably carried out in base, e.g. dimethylaniline or pyridine.

Process (n) may be carried out in the usual manner using a halogenating agent, e.g. phosphorus trichloride or tribromide, phosphorous pentachloride or thionyl chloride.

Reduction process (o) may be carried out using a reducing agent which reduces acids to alcohols e.g. a hydride such as borane.

The starting materials of formula II used in process (a) are known compounds or can be prepared by analogous methods e.g. by reducing an amide of formula Ar—A—NHCO—$E^1$ where $E^1$ has one $CH_2$ group less than E.

Compounds of formula V can be prepared by acylating a corresponding compound of formula Ar—A—N-H—B—$D^1$ using an acid chloride of formula $R^4$ COCl. Compounds of formula Ar—A—NH—B—$D^3$ can themselves be prepared by alkylating amines of formula $NH_2$—B—$D^3$ using a halide of formula Ar-A-hal.

Compounds of formula VI can be prepared by acylating amines of formula Ar-A-NH-E using 'an acid chloride of formula ClCO.$B^1$-$D^2$ wherein the variables have the values defined in connection with process (d).

Compounds of formula VII may be prepared by a process analogous to process (a) above using a compound of formula II and compound of formula hal—B—$D^3$.

Compounds of formula VIII may be prepared by reacting a compound of formula IX:

(IX)

with a compound of formula $T^1CH_2T^2$, eg a malonic acid ester in the presence of a base, e.g. sodium hydride or sodium ethoxide. The compound of formula IX may itself be prepared by reaction of phosphorus tribromide and a compound of formula I wherein D is —$CH_2OH$.

Starting materials for the processes described herein are known compounds or can be prepared by analogous methods for known compounds.

In any of the aforementioned reactions compounds of formula (and Ia) may be isolated in free base form or as acid addition salts as desired. Examples of such salts include salts with pharmaceutically acceptable acids such as hydrochloric, hydrobromic, hyroiodic, sulphuric, phosphoric, nitric, acetic, citric, tartaric, fumaric, succinic, malonic, formic, maleic acid or organosulphonic acids such as methane sulphonic or tosylic acid.

When acidic substituents are present at as also possible to form salts with bases e.g. alkali metal (such as sodium) or ammonium salts e.g. trimethylammonium. Such salts of the compounds of formula I and Ia are included within the scope of this invention.

This invention also provides pharmaceutical compositions comprising a compound of formula Ia or a pharmaceutically acceptable salt thereof and a pharmaceutically acceptable carrier.

For the pharmaceutical compositions any suitable carrier known in the art can be used. In such a composition, the carrier may be a solid, liquid or mixture of a solid and a liquid. Solid form compositions include powders, tablets and capsules. A solid carrier can be one or more substances which may also act as flavouring agents, lubricants, solubilisers, suspending agents, binders, or tablet disintegrating agents, it can also be encapsulating material. In powders the carrier is a finely divided solid which is in admixture with the finely divided active ingredient. In tablets the active ingredient is mixed with a carrier having the necessary binding properties in suitable proportions and compacted in the shape and size desired. The powders and tablets preferably contain from 5 to 99, preferably 10–80% of the active ingredient: Suitable solid carriers are magnesium stearate, talc, sugar, lactose, pectin, aextrin, starch, gelatin, tragacanth, methyl cellulose, sodium carboxymethyl cellulose, a low melting wax and cocoa butter. The term "composition" is intended to include the formulation of an active ingredient with encapsulating material as carrier, to give a capsule in which the active ingredient (with or without other carrier) is surrounded by carriers, which is thus in association with it. Similarly cachets are included.

Sterile liquid form compositions include sterile solutions, suspensions, emulsions, syrups, and elixirs.

The active ingredient can be dissolved or suspended in a pharmaceutically acceptable carrier, such a sterile water, sterile organic solvent or a mixture of both. The active ingredients can often be dissolved in a suitable organic solvent, for instance aqueous propylene glycol containing from 10 to 75% of the glycol by weight is generally suitable. Other compositions can be made by dispersing the finely-divided active ingredient in aqueous starch or sodium carboxymethyl cellulose solution, or in a suitable oil, for instance arachis oil. The composition may be administered orally, nasally, rectally or parenterally.

Preferably the pharmaceutical composition is in unit dosage form, the composition is sub-divided in unit doses containing appropriate quantities of the active ingredient the unit dosage form can be a packaged composition, the package containing specific quantities of compositions, for example packeted powders or vials or ampoules. The unit dosage form can be a capsule, cachet or tablet itself, or it can be the appropriate number of any of these in packaged form. The quantity of active ingredient in a unit dose of composition may be varied or adjusted from 1 to 500 mg or more, e.g. 25 mg to 250 mg, according to the particular need and the activity of the active ingredient. The invention also includes the compounds in the absence of carrier where the compounds are in unit dosage form. Based on the results from animal studies the dosage range for the treatment of humans using a compound of formula I will be in the range from about 1 mg to 2 g per day depending on the activity of the compound.

The following Examples illustrate the invention and methods for preparing compounds of the invention.

EXAMPLE 1

4-[N,N-Bis-(4-Chlorobenzyl)amino]butyronitrile

Bis-(4-chlorobenzyl)amine hydrochloride [prepared by reducing N-(4-chlorobenzyl)-4-chlorobenzamide with lithium aluminium hydride in tetrahydrofuran] was basified using sodium carbonate in methylene dichloride solvent to give after rotary evaporation 3.16 g of the free base as an oil. This was then mixed with 4-bromobutyronitrile (1.19 ml), diisopropylethylamine (2.1 ml) and 25 ml of dry dimethylformamide and the mixture stirred at 80° C. under nitrogen for 24 hours. On cooling water (100 cm$^3$) was added and then the mixture was extracted with 1×50 ml and 2×25 ml of methylene dichloride. The combined extracts were washed with water, dried (MgSO$_4$), filtered and evaporated to give an oil. This was further purified by column chromatography (silica column eluted with toluene) to give 2.83 g of the title product as an oil. 2.8 g of the title compound was dissolved in 10 ml hot ethanol, acidified with 0.76 g (1 equiv) of oxalic acid, diluted with ether and cooled to give, after filtration, the 1:1-ethanedioate salt (1.78 g) as colourless crystals, mp 124°-6° (dec).

Analysis $C_{18}H_{18}Cl_2N_2.C_2H_2O_4$ requires: C,56.8; H,4.8; N,6.6 Found: C, 57.0; H, 4.9; N,6.2%.

EXAMPLE 2

4-[N,N-Bis-(4-Chlorobenzyl)amino]butyric acid 1.36 g of 4-[N,N-bis-(4-chlorobenzyl)amino]butyronitrile (as produced in Example 1), water (25 ml) and concentrated hydrochloric acid (10 ml) were stirred and heated to reflux for 5½ hours under a nitrogen blanket. After cooling, an oil was obtained which crystallised on scratching. The crystals were filtered, washed with dilute hydrochloric acid, then with diethyl. ether and recrystallised from isopropanol ether. Filtration and drying at 60° /1 mm Hg gave the title compound as the hydrochloride salt (0.32 g) m.p. 206°-208° C.(dec)

Analysis $C_{18}H_{19}NO_2.HCl$ requires C,55.6; H,5.2; N,3.6 Found: C55.4; H,5.2; N,3.7%.

EXAMPLE 3

4-[N,N-Bis-(4-chlorobenzyl) amino]butyramide

A solution of 4-[N,N-Bis-( 4-chlorobenzyl)amino]-butyronitrile (2.0 g) prepared according to Example 1 in dichloromethane (10 ml) was cooled in ice, then treated with the phase-transfer catalyst $^n$Bu$_4$.NHSO$_4$ (0.5 g), 20% aq NaOH (3.2 ml) and 30% H$_2$O$_2$ (4.0 ml). The mixture was stirred vigorously at 0° for about half an hour, then at room temperature for 23 hours. After dilution with dichloromethane the layers were separated, and the organic phase washed with water and with dil. aq. NaHSO$_3$, then dried (MgSO$_4$). Filtration and evaporation gave a syrup (2.26 g) which was flash-chromatographed on neutral alumina eluted with neat toluene (to remove starting material (0.3 g) and then with 10% EtOH-toluene to recover the product (1.62 g). Repeat chromatography on silica eluted with 2-5% EtOH-toluene gave the title compound (1.55 g; 73.6%) as a syrup which set solid on standing. The resulting crystals had m.p. 66°-76°.

Analysis $C_{18}H_{20}N_2OCl_2$ requires: C, 61.6; H, 6.0; N, 8.0 Found: C, 61.5; H, 5.8; N, 8.0%.

EXAMPLE 4

4-(N,N-Dibenzylamino]butyramide a) By a method analogous to Example 1 dibenzylamine was reacted with 4-bromobutyronitrile to give 4-(N,N-dibenzylamino)butyronitrile, mp. 45°-46° C. b) Hydrogen peroxide (30% w/v; 5.6 ml), tetra-n-butylammonium hydrogensulphate (1.70 g) and 5N aqueous sodium hydroxide (4 ml) were added to a stirred solution of 4-(N,N-dibenzylamino)butyronitrile (2.64 g) in dichloromethane (10 ml) with water cooling. The mixture was stirred vigorously at room temperature for 17 hours and dichloromethane (100 ml) was added. The layers were separated and the organic phase was washed with saturated aqueous sodium chloride (10 ml), dried (Na$_2$SO$_4$) and concentrated in vacuo to give a viscous oil (4.12 g). The product was chromatographed on silica with eluant 20% ethyl acetate/toluene →ethyl acetate and recrystallised from cyclohexane to give the title compound (1.86 g, 66%), m.p. 76°-77° C.

Analysis $C_{18}H_{22}N_2O$ requires: C, 76.55; H. 7.85, N, 9.9 Found: C, 76.45; H, 7.95; N, 9.8%

EXAMPLE 5

4-(N,N-Dibenzylamino)butyric acid

A solution of 4-CN,N-dibenzylamino)butyronitrile (2.64 g) in concentrated hydrochloric acid (50 ml) was refluxed for 3 hours. The solution was concentrated in vacuo to give a solid, which was recrystalised from acetic acid and water to give the title compound as the monohydrochloride monoacetic acid salt (1.84 g), m.p. 138°-139° C.

Analysis $C_{18}H_{21}NO_2.HCl. C_2H_4O_2$ requires: C, 63.25; H, 6.9; N, 3.7% Found: C, 63.6; H, 7.2; N, 3.9

EXAMPLE 6

4-[N,N-Bis(4-methylbenzl)amino]butyronitrile

A solution of 4-bromobutyronitrile (14.80 g) in dry dimethylformamide ( 100 ml ) was added dropwise over 15 minutes to a stirred solution of bis-(4-methylbenzyl)amine(22.53 g) and N,N-diisopropylethylamine (35 ml 26 g ) in dry dimethylformamide ( 100 ml ). The solution was heated (oil bath 115° C.) under nitrogen for 4 hours. The solution was poured onto a mixture of water (400 ml) and saturated aqueous sodium chloride (400 ml) and the mixture was extracted with ether (2×200 ml). The extracts were dried (Na$_2$SO$_4$) and concentrated in vacuo to give an orange oil (39.55 g). The product was chromatographed on silica with eluant diisopropyl ether, and dried at 100° C. at 0.1 mmHg for 4 hours to give 4-[N,N-bis(4-methylbenzyl)amino]butyronitrile (26 g, 89%), which was used in Example 7 without further characterisation.

EXAMPLE 7

4-[N,N-Bis-(4-methylbenzyl)amino]butyramide

Hydrogen peroxide (30% w/vl 5.67 ml), tetra-n-butylammonium hydrogensulphate (70 g) and 5N aqueous sodium hydroxide (4 ml) were added successively to a stirred solution of 4-(N,N-bis-(4-methylbenzyl)amino]butyronitrile (2.93 g) in dichloromethane (10 ml), with water cooling.

The mixture was stirred vigorously at room temperature for 16 hours then dichloromethane (100 ml) was added. The layers were separated and the organic phase was washed with saturated aqueous sodium chloride (1×10 ml), dried (Na$_2$SO$_4$) and concentrated in vacuo to give a viscous oil (4.61 g). The product was chromatographed on silica with eluant 20% ethyl acetate/toluene→ ethyl acetate and triturated with cyclohexane to give the title compound (1.77 g), m.p. 85°–86° C.

Analysis (Found: C,77.25; H, 8.35; N, 9.25; C$_{20}$H$_{26}$N$_2$O requires C, 77.4; H, 8.45; N, 9.0%.

EXAMPLE 8

4-[N,N-Bis-(4-methylbenzyl)amino]butyric acid

4-[N,N-Bis-(4-methyl benzyl)amino]butyronitrile (2.93 g) was suspended in concentrated hydrochloric acid (50 ml) and the mixture was refluxed (oil bath 130° C.) for 4 hours. The solution was concentrated in vacuo to give a foam (4.17 g). The product was triturated with hot water and crystallised in ether at −78° C. to give the title compound as the hydrochloride, three quarters hydrate (2.82 g), m.p. 148°–151° C.

Analysis C$_{20}$H$_{25}$NO$_2$.HCl.0.75H$_2$O requires: C, 66.45; H, 7.65; N, 3.9. Found: C, 66.2; H, 7.2; N, 3.95%.

EXAMPLE 9

4-[N, N-Bis-(3,4-Dichlorobenzyl)amino]butyronitrile

Using a procedure analogous to Example 6, Bis-(3,4-dichlorobenzyl)amine (2.71g, 8.09mM) was reacted with 4-bromobutyronitrile (0.81ml) to give the title compound as an oil 1.97g. Ir (film) CN 2230cm$^{-1}$.

EXAMPLE 10

4-[N,N-Bis-(3,4-dichlorobenzyl)amino]butyric acid

A mixture of 4-[N,N-bis-(3,4-dichlorobenzyl)amino]-butyronitrile (1.95g), NaOH (2.0g) and ethanol (25ml) was stirred and heated to reflux for 6 hours under a nitrogen blanket. After cooling, the solvent was evaporated in vacuo to give a paste which was taken up in water (30ml), acidified with conc. HCl, stirred well and cooled in ice. The oil which had precipitated crystallised slowly. The crystals were filtered off, washed well with water, and recrystallised from dimethylformamide, diluted with a large volume of ether. The precipitated oil again crystallised slowly. The crystals were triturated with hot isopropanol, diluted with ether, collected by filtration and dried at 50°/1 mm to give the title compound as the hydrochloride salt. (1 .20g), m.p. 227–231° (decomp).

Analysis C$_{18}$H$_{17}$NO$_2$Cl$_4$. HCl requires: C, 47.2; H, 4.0; N, 3.1 Found: C, 47.2; H, 4.0; N, 3.2%.

EXAMPLE 11

4- [N, N-Bis-(4-methoxybenzyl)amino]butyronitrile

A solution of 4-bromobutyronitrile (14.80g) in dry dimethylformamide (100 ml) was added dropwise over 15 minutes to a stirred solution of bis-(4-methoxybenzyl)amine (25.73g) and N,N-diisopropylethylamine (35 ml, 26 g) in dry dimethylformamide (100 ml ). The yellow solution was heated under nitrogen at 110° C. for 4 hours and was allowed to cool. The solution was poured onto a mixture of water (400 ml) and saturated aqueous sodium chloride (400 ml ) and then extracted with ether (2×200 ml). The extracts were dried (Na$_2$SO$_4$) and concentrated in vacuo to give an oil (35.93 g). The product was chromatographed on silica with eluant diisopropyl ether, and was triturated with cyclohexane to give the title compound (26.00g), m.p. 56°–58° C.

Analysis

C$_{20}$H$_{24}$N$_2$O$_2$ requires:C, 74.05; H, 7.45; N, 8.65. Found: C, 73.85, H 7.4; N, 8.85%.

EXAMPLE 12

4- [N, N-Bis-(4-Methoxybenzy 1 ) amino]butyramide

Hydrogen peroxide (30% w/v; 5.67 ml ), tetra-n-butylammonium hydrogensulphate (1.70 g) and 5N aqueous sodium hydroxide (4 ml) were added successively to a stirred solution of 4-[N,N-bis-(4-methoxybenzyl)amino]butyronitrile (3.24 g) in dichloromethane (10 ml), with water cooling. The mixture was stirred vigorously at room temperature for 18 hours and dichloromethane (100 ml) was added. The layers were separated and the organic phase was washed with saturated aqueous sodium chloride (1×10 ml), dried (Na$_2$SO$_4$) and concentrated in vacuo to give an oil (4.71 g). The product was chromatographed on silica with eluant 20% ethyl acetate/toluene→ethyl acetate, and crystallised from diisopropyl ether at room temperature to give the title compound (2.21g), m.p. 53°–54° C.

Analysis:

C$_{20}$H$_{26}$N$_2$O$_3$ requires :C, 70.15; H, 7.65; N, 8.2%. Found: C, 70.0; H, 7.75; N, 8.15%.

EXAMPLE 13

5 - ( N,N-Dibenzylamino)pentanonitrile

A solution of 5-bromopentanonitrile (16.20 g) in dry dimethylformamide (100 ml) was added dropwise over 15 minutes to a stirred solution of dibenzylamine (19.73 g) and N,N-diisopropylethylamine (35 ml 26 g) in dry dimethylformamide (100 ml). The solution was heated (oil bath 110° C.) for 4 hours and was allowed to cool. The solution was poured onto a mixture of saturated aqueous sodium chloride (400 ml) and water (400 ml) and the mixture was extracted with ether (2×200 ml). The extracts were dried (Na$_2$SO$_4$) and concentrated in vacuo to give a mobile oil (30.32 g). The oil was chromatographed on silica with eluant diethyl ether to give the title compound (23.17 g) as an oil which was used without further purification in Example 14.

EXAMPLE 14

5-(N,N-Dibenzylamino)pentanoic acid

A solution of 5-(N,N-dibenzylamino)pentanonitrile (2.75 g) in concentrated hydrochloric acid (50 ml) was refluxed (oil bath 140° C.) for 4 hours. The solution was allowed to cool, and the product crystallised. The mixture was concentrated in vacuo to give a white solid which was recrystallised from water, filtering out insoluble material, to give the title compound (2.96 g), m.p. 202°–205° C. .

Analysis

C$_{19}$H$_{23}$NO$_2$.HCl requires:C, 68.35; H, 7.25; N, 4.2. Found: C, 68.15; H, 7.35; N, 4.2%.

EXAMPLE 5

4-N,N-(Bis-[2 (4-chlorophenyl)ethyl]amino)butyronitrile

In a manner analogous to Example 6, 5.08 g of bis-[2-(4-chlorophenyl )ethyl]amine was reacted with 1.73 ml 4-bromobutyronitrile to give the title compound (5.83g).

EXAMPLE 16

4-N,N-(Bis-[2-(4-chlorophenyl )ethyl]amino)butyric acid

A solution of the 4-(bis-[2-(4-chlorophenyl )ethyl]amino)butyronitrile (5.8g) and NaOH (5.7g) in ethanol (75 ml) was stirred and heated to reflux for 6 hours and, after cooling, the solvent was evaporated and the residue was taken up in water, acidified with conc. HCl and the turbid mixture maintained at 5° C. overnight, during which time an oil precipitated and solidified. The solid was collected by filtration and washed with water. It was then boiled for 1 hour with conc. HBr, cooled, kept at 5° until resolidification had occurred, and the solid was collected by filtration. Recrystallisation was twice effected by dissolution of the solid in hot isopropanol containing a few drops of water, followed by dilution with ether, to give crystals of the title compound as the hydrobromide salt, (4.03 g), m.p. 150°-2° (dec.; "sweating"0 occurs above 147° ).

Analysis:

$C_{20}H_{23}NO_2Cl_2.HBr$ requires: C,52.1 ;H,5.2;N,3.0 Found: C,52.2;H,5.4;N,3.25%

EXAMPLE 17

Ethyl 4-[N,N-bis-(4-chlorobenzyl)amino]butanoate a) An ice-cooled, stirred suspension of 4-[N,N-bis-(4-chlorobenzyl)amino]butyric acid, hydrochloride salt (2.05 g) (prepared according to Example 2) in absolute ethanol (100 ml) was treated with HCl gas for ½ hour. The solution was warmed to room temperature and allowed to stand overnight. The solvent was evaporated in vacuo, and the oily residue taken up in aqueous $NaHCO_3$ and extracted with dichloromethane (2×25 ml). The combined extracts were washed with water and dried ($MgSO_4$). Filtration and evaporation gave an oil (1.86 g) which was freed from residual acid by passage through a silica column, eluted with ethyl acetate. Evaporation of the eluate gave an oil (1.32 g) which was dissolved in ethanol (5 ml) and treated with oxalic acid (0.30 g; 1 equiv.). Evaporation of the solvent and treatment of the residue with hot ethyl acetate caused crystallisation to occur. The crystals were collected by filtration and recrystallised from ethanol-ethyl acetate to give the title compound as the 1:1 ethanedioate salt (0.53 g) as colorless crystals, m.p. 123.5°-125°.

Analysis $C_{20}H_{23}NO_2Cl_2.C_2H_2O_4$ requires: C,56.2;H,5.4;N,3.0 Found: C,56.3;H,5.5;N,2.7% b) The product of step (a) is converted to 4-[N,N-bis-(4-chlorobenzyl)amino] butyramide by treatment with ammonium hydroxide.

EXAMPLE 18

4- [N,N-Bis-(4-Chlorobenzyl)amino)butanol

A stirred suspension of 4-[N,N-bis-(4-chlorobenzyl)amino]butyric acid, hydrochloride (prepared according to Example 2) (13.44 g) in dry tetrahydrofuran (250 ml) was stirred and heated to reflux as borane-methyl sulphide (10 molar; 17 ml; 5 equiv.) was added dropwise. The mixture was stirred and heated to reflux under a nitrogen blanket for 17 hours. After cooling, the mixture was decomposed by the dropwise addition of 10% aq $H_2SO_4$. The organic solvent was evaporated in vacuo and the aqueous residue was diluted with 10% aq $H_2SO_4$(120 ml) and heated to reflux for 3 hours.

The cooled solution was poured onto aqueous $Na_2CO_3$ and brine and extracted with dichloromethane (2×100 ml). The combined extracts, which showed a tendency to emulsify in the presence of water, were washed with brine and dried ($MgSO_4$). Filtration and evaporation gave a viscous syrup (11.38 g) which was purified by passage through silica gel, eluted with neat toluene and then with 2-5% ethanol/toluene to give an oil (9.40 g). .

A solution of the oil (7.50 g) in hot ethanol (25 ml) was treated with 2.58 g (1 equiv) of fumaric acid. The crystals which separated overnight were triturated with boiling iso-propanol, cooled and refiltered, to give crystals of the title compound as the 1½ fumaric acid salt (3.70 g) m.p. 141-143° (dec).

Analysis $C_{18}H_{21}NOCl_2.1\frac{1}{2} C_4H_4O_4$ requires: C,56.3;H,5.3;N,2.7 Found: C, 56.0; H,5.4; N, 2.6%

EXAMPLE 19

(a)

4-[(N-(1,1-diphenyl )methyl-N-benzyl)amino]butyronitrile

A solution of 4-bromobutyronitrile (7.40 g) in dry dimethylformamide (50 ml) was added dropwise over 5 minutes to a stirred solution of N-benzyl-1,1-diphenylmethylamine (13.67 g)(prepared by reductive amination of benzophenone and benzylamine using sodium cyanoborohydride) and N,N-diisopropylethylamine (18 ml, 13 g) in dry dimethylformamide (50 ml). The solution was heated at 120° C. under nitrogen for 42 hours and was poured onto a mixture of saturated aqueous sodium chloride (200 ml) and water (200 ml). The mixture was extracted with ether (2×100 ml) and the extracts were dried ($Na_2SO_4$) and concentrated in vacuo to give an oil (21.27 g). The product was chromatographed on silica with eluant dichloromethane. Fractions containing the desired material were evaporated to dryness at reduced pressure and dried at 110° C. at 0.1 mmHg for 4 hours to give 4-[(N-(1,1-diphenyl)methyl-N-benzyl)amino]-butyronitrile as an oil (14.61 g).

(b)

4-[(N-(1,1-Diphenyl)methyl-N-benzyl)amino]butyric acid

A solution of the product of step (a) (3.40 g) in absolute ethanol (100 ml) was treated with sodium hydroxide pellets (20.0 g). The mixture was refluxed for 4 hours and was concentrated in vacuo to give a solid. Water (200 ml) and ice (200 ml) were added and the mixture was acidified with concentrated hydrochloric acid (100 ml) at 0° C. The mixture was concentrated in vacuo and the residue was triturated with isopropanol. The mixture was filtered and the solution was reconcentrated to give a foam (4.51 g). The product was dissolved in hot water and the mixture was filtered through kieselguhr. The filtrate was concentrated in vacuo to give a solid (2.21 g), which was triturated with ethyl acetate, to give the title compound as the hydrochloride three quarters hydrate (1.90 g.), m.p. 166°-173° C.

Analysis $C_{24}H_{25}NO_2.HCl.0.75H_2O$ requires C, 70.4; H, 6.75; N, 3.4. Found: C,70.65; H, 6.8; N, 3.05%.

EXAMPLE 20 a) 4-[N,N-Bis-(3-bromobenzyl)amino]butyronitrile

A mixture of N,N-bis-(3-bromobenzyl)amine (13.47 g; 0.038 mol), 4-bromobutyronitrile (3.77 ml; 0.038 mol), diisopropylethylamine (10 ml; 0.057 mol), potassium iodide (1 g) and dimethylformamide (30 ml) was stirred under a nitrogen blanket at 80°-90° for 22 hours. After cooling, the solvent was evaporated and the residue was taken up in aq. $Na_2CO_3$ and extracted with dichloromethane. The combined extracts were washed with aq. $Na_2CO_3$ and dried ($MgSO_4$). Filtration and evaporation gave an oil (18.49 g), which was chromatographed on silica eluted with 1% v/v ethanol-toluene. Evaporation of fractions containing product gave the title compound (12.36 g; 77.2%) as an oil. A solution of the product (0.84 g; 2 mmol) in hot ethanol (5 ml) was treated with oxalic acid (0.18 g; 2 mmol). Crystallisation occurred overnight and the crystals were collected by filtration and recrystallised from ethanol-ether to give the 1:1 ethanedioate salt (0.22 g), m.p. 120°-122° C.

Analysis $C_{18}H_{18}Br_2N_2 \cdot (COOH)_2$ requires: C, 46.9; H, 3.9; N, 5.5. Found: C,47.1; H,4.1; N, 5.3%.

b) 4-[N,N-Bis-(3-bromobenzyl)amino]butyric acid

A solution of 4-[N,N-bis-(3-bromobenzyl)amino]-butyronitrile (12 g) and ethanol (120 ml) was stirred and heated to reflux for 17.5 hours under nitrogen. After cooling, the solvent was evaporated in vacuo. The residue was taken up in water (120 ml) and strongly acidified with conc. HCl (36 ml). The mixture was cooled in ice, causing an oil to precipitate. The oil crystallised after standing overnight and was filtered off and triturated with hot isopropanol. After cooling, the crystals were collected by filtration and washed with ether to give crystals of the title compound as the hydrochloride salt (10.87 g), m.p. 156°-159° C.

Analysis $C_{18}H_{19}Br_2NO_2 \cdot HCl$ requires: C, 45.3, H, 4.2; N, 2.9 Found: C,45.0; H,4.5; N, 2.5%

EXAMPLE 21 a) 4-[N,N-Bis-(3-chlorobenzyl)amino]butyronitrile

A mixture of bis-(3-chlorobenzyl)amine (8.0g; 0.03 mol), potassium iodide (5.0 g; 0.03 mol), diisopropylethylamine (7.0 ml; 0.04 mol), 4-bromobutyronitrile (3.0 ml; 0.03 mol) and dimethylformamide (25 ml) was stirred and heated to an oil-bath temperature of 80° C. for 18 hours, under a nitrogen blanket. After cooling, the solvent was evaporated and the residue taken up in dilute aqueous $Na_2CO_3$ and extracted with dichloromethane (3×50 ml). The combined extracts were washed with water and dried ($MgSO_4$). Filtration and evaporation gave an oil (11.0 g) which was chromatographed on silica eluted with neat toluene and then with 2% v/v ethanol-toluene. The fractions containing product were collected and evaporated to give the title compound as an oil (8.59 g).

A portion (1.1 g) of the oil was converted to the 1:1 ethanedioate salt by addition of oxalic acid (one equivalent) in isopropanol. After evaporation of the solvent, the 1.1 ethanedioate salt of the title compound was obtained by crystallisation from ethyl acetate, m.p. 74°-9° C.

Analysis $C_{18}H_{18}Cl_2N_2 \cdot (COOH)_2$ requires: C,56.7; H,4.8; N,6.6 Found: C,56.3; H,4.6; N,6.7% b) 4-[N,N-Bis-(3-chlorobenzyl)amino)]butyric acid

A solution of 4-[N,N-bis-(3-chlorobenzyl)amino]-butyronitrile (8.59 g; 0.026 mol), NaOH (10 g; 0.25 mol) and ethanol (125 ml) was stirred and heated to reflux for 18 hours. After cooling the solvent was evaporated in vacuo and the solid residue taken up in water (75 ml). After further cooling in ice, conc. HCl was added until the mixture was strongly acid (ca. 25 ml required). The initially precipitated oil hardened to a solid, which was collected by filtration and recrystallised from dimethylformamide-ether and then from 10% v/v water-isopropanol followed by dilution with ether. After drying at 45° C./1 mm the hydrochloride hemihydrate salt of the title compound was obtained (5.60g). m.p. 170°-173° (dec.; softens above 166°).

Analysis $C_{18}H_{19}Cl_2NO_2 \cdot \frac{1}{2}H_2O$ requires: C,54.4; H,5.3; N,3.5 Found C, 54.4; H,5.2; N,3.5%.

EXAMPLE 22

4-[N,N-Bis-(2-thienylmethyl)amino]butyric acid a) In a manner analogous to Example 21 a, 4-[N,N-bis-(2-thienylmethyl)amino]butyronitrile was prepared by alkylation of bis-(2-thienylmethyl)amine using 4-bromobutyronitrile.

b) In a manner analogous to Example 2 4-[N,N-bis-(2-thienylmethyl)amino]butyronitrile (12 g) was hydrolysed using concentrated hydrochloric acid (200 ml) to give the title compound as an oily-solid residue. Isopropanol (150 ml) was added and the mixture cooled with stirring. Precipitated $NH_4Cl$ was removed by filtration and the filtrate was concentrated and filtered to remove further inorganic material. The filtrate was partitioned between aqueous NaOH and toluene. After standing overnight, the layers were separated, the aqueous phase was acidified to pH1, concentrated in vacuo, diluted with isopropanol, filtered to remove precipitated NaCl and evaporated to dryness to give a solid.

The solid was chromatographed on silica eluted with 2% v/v ethanol-toluene, then with 10%- and 20%- v/v ethanol-toluene. The product-bearing fractions were evaporated, dissolved in isopropanol, filtered to remove a little solid material, concentrated in vacuo and diluted with ether. The initially-precipitated gum crystallised after standing for 72 hours. The solid was collected by filtration, purified by trituration with boiling isopropanol, cooled and refiltered to give crystals of the title compound, as the hydrochloride salt mp 158°-160°.

Analysis:

$C_{14}H_{17}NO_2S_2 \cdot HCl$ requires C, 50.7; H, 5.5; N, 4.2% Found C,50.5; H,5.6; N,4.1%

EXAMPLE 23

4-[(N-4-Methylphenylmethyl-N-phenylmethyl)amino]-burytic acid a) In a manner analogous to Example 21a, 4-[(N-4-methylphenylmethyl-N-phenylmethyl)amino]-butyronitrile was prepared by alkylation of N-(4-methylphenylmethyl)benzenemethanamine (4.22 g) using 4-bromobutyronitrile (2 ml). Yield 4.45 g.

b) In a manner analogous to Example 10 the nitrile from step (a) above was hydrolysed using NaOH in ethanol to give, after acidification with HBr, the title compound as the hydrobromide, quarterhydrate salt, mp 119°-125° C.

Analysis $C_{19}H_{23}NO_2 \cdot HBr \cdot \frac{1}{4}H_2O$ requires. C, 59.6; H,6 5; N, 3.7 Found: C, 59.5, H, 6 75; N, 3.5%.

EXAMPLE 24

4-[N, N-Dibenzyl]amino-N'N'-dimethylbutyramide

A sample of 4-[N-N-dibenzyl]aminobutyric acid (8.51 g, 0.03 moles) (prepared according to Example 5) was dissolved in dry acetonitrile (50 ml) under nitrogen. 1,1'-Carbonyldiimidazole (4.85 g) was dissolved in dry acetonitrile and added dropwise over 1 hour. The mixture was stirred under nitrogen for 96 hours. An excess of dimethylamine (10 g. 0.22 moles) was added, and the mixture stirred for a further two hours. Evaporation gave a residue which was separated on a silica column with ethyl acetate as eluant. Ten 50 ml fractions were collected; the product appearing in fractions 5-8. Evaporation gave an oil which was dissolved in ether. Acidification with ethereal HCl to pH1 gave a precipitate which was recrystallised from ethyl acetate/isopropanol to give crystals of the title compound as the hydrochloride, quarterhydrate, mp. 166-171.

Analysis $C_{20} H_{26} N_2O \cdot HCl \cdot \frac{1}{4}H_2O$ requires C, 68.5; H,7.9; N,8.0. Found C, 68.7; H, 8.0; N, 8.0%

EXAMPLE 25

4-[N,N-Bis-(1-Naphthalenemethyl)amino]butyric acid a) 1-Naphthoyl chloride (5.0 g, 0.026. moles) in $CH_2Cl_2$ (25 ml) was added dropwise to a stirred solution of ice cooled 1-naphthalenemethylamine in $CH_2Cl_2$ (25 ml). A white precipitate formed immediately. The mixture was stirred at room temperature for 3 hours then filtered. The precipitate was washed with water and hot ethanol, then dried to give N-(1-naphthalenylmethyl) 1-naphthaleneacetamide (5.18 g, 0.017 moles). The amide (5.18 g) was dissolved in tetrahydrofuran (25 ml) then added dropwise to $LiAlH_4$(0.63 g 0.016 moles) in tetrahydrofuran (25 ml). The mixture was heated at reflux for 24 hours, then worked up by dropwise addition of water (0.6 ml), 15% aq NaOH(0.6 ml) and water (1.9 ml). Filtration, drying ($MgSO_4$) and evaporation gave an oil (22.5 g) which was crystallised from ice-cold ethanol to give N,N-bis-(1-naphthalenemethyl)amine (2.54 g)

(b) The amine from step (a) (2.54 g) was dissolved in DMF (20 ml), then 4-bromobutyronitrile (0.76 ml, 0.0076 moles) and diisopropylethylamine (4.07 ml 0.023 moles) in DMF (25 ml) added dropwise. Potassium iodide (1 g) was added and the mixture heated at reflux for 24 hours. Evaporation gave a solid which was taken up into $Na_2CO_3$ (50 ml), extracted into $CH_2Cl_2$ (3×25 ml) dried ($MgSO_4$) and evaporated to give a solid. Separation on a silica column with 10% v/v ethyl acetate in toluene as eluant, followed by evaporation, gave 4-[N,N-bis(1-naphthalenemethyl)amino]butyronitrile (1.54 g).

(c) The nitrile from step (b) (1.54 g) was dissolved in isopropanol (25 ml), then NaOH (1.0 g, 0.024 moles) was added and the mixture heated at reflux for 24 hours. Evaporation gave a residue which was taken up into water and extracted with $CH_2Cl_2$ (3×30 ml). Drying and evaporation gave a solid which was partially dissolved in ether, then precipitated with ethereal HCl. Filtration, trituration with HCl followed by ice-cold water gave the title compound as the hydrochloride hemihydrate, (1.62 g) m.p. 187°-191° C.

Analysis $C_{26} H_{25} NO_2 \cdot HCl \cdot \frac{1}{2}H_2O$ requires: C, 72.8; H,6.4; N,3.3. Found: C, 72.7 ; H, 6.6; N, 3.5%.

EXAMPLE 26

4-[N-(p-Chlorobenzyl)-N-methylamino]butyramide

A solution of 4-[N-(p-chlorobenzyl)-N-methylamino]butyronitrile (0.95 g; 4.27 mmol) in dichloromethane (5 ml) was cooled in ice as $^nBu_4NHSO_4$ (0.3 g) was added, followed quickly by 20% w/v aq NaOH (1.6 ml) and 30% hydrogen peroxide (2.0 ml). The mixture was stirred vigorously, briefly at 0° C. and then at room temperature, for 2 hours. After dilution with more dichloromethane, the layers were separated, the organic phase was washed with water and dried ($MgSO_4$). Filtration and evaporation gave an oil (0.83 g) which was chromatographed on silica eluted with toluene containing an increasing proportion of isopropanol 50% v/v). The product was obtained as an oil (0.52 g) which set solid on standing, to give the title compound (0.52 g) m.p. 62°-64°.

Analysis $C_{12} H_{17} ClN_2O$ requires: C, 59.9; H, 7.1; N, 11.6 Found: C, 60.0; H, 7.1; N, 11.9%

EXAMPLE 27

4-[N-Methyl-N-(4-chlorobenzyl)amino]butyric acid

A mixture of 4-[N-methyl-N-(4-chlorobenzyl)amino]-butyronitrile (4.65 g; 0.021 mol) and NaOH (5 g; 0.125 mol) in ethanol (50 ml) was stirred and heated to reflux under a nitrogen blanket for 21 hours. The solvent was evaporated to give a paste, which was dissolved in water (50 ml) and strongly acidified with conc. HCl (ca. 12 ml). The solvents were again evaporated, and the residual, semi-crystalline mass was boiled briefly with isopropanol, filtered, and the inorganic precipitate washed well with isopropanol. The filtrate was evaporated to give a syrup (7.47 g) which was crystallised in several crops from isopropanol/ether. The combined crops were triturated with boiling isopropanol, cooled filtered and dried at 50°/1 mm to give the title compound as the hydrochloride salt (4.22 g) m.p. 149°-152°.

Analysis $C_{12} H_{16} ClNO_2 \cdot HCl$ requires C, 51.8; H, 6.2; N, 5.0 Found: C, 51.5; H, 6.2; N ,5.0%.

EXAMPLE 28

In a manner analogous to Examples 26 and 27, nitriles of formula X shown below were hydrolysed to the corresponding acids or partially hydrolysed to the amide as shown below:

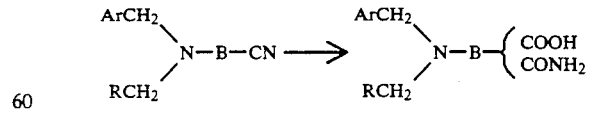

in which formulae Ar, R and B represent:

| Ar | R | B |
| --- | --- | --- |
| 2-furanyl | 2-furanyl | —$(CH_2)_3$— |
| 2-furanyl | hydrogen | —$(CH_2)_3$— |
| 3-pyridyl | 3-pyridyl | —$(CH_2)_3$— |
| 3-quinolyl | 3-quinolyl | —$(CH_2)_3$— |

| Ar | R | B |
|---|---|---|
| 2-thiazolyl | 2-thiazolyl | —(CH$_2$)$_3$— |

We claim

1. A compound of formula Ia

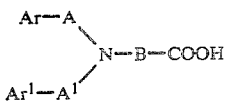

or a pharmaceutically salt thereof, wherein

Ar and Ar$^1$ are the same or different mono- or bicyclic carbocyclic aryl groups of 6 to 10 carbon atoms, Ar and Ar$^1$ being each, independently, optionally substituted by one or more substituents selected from lower alkyl, lower alkoxy, halogen, haloloweralkyl, haloloweralkoxy, cyano, amino, lower alkylamino, di-loweralkylamino and nitro;

A and A$^1$ are the same of different alkylene grouped having one or two carbon atoms linking Ar or Ar$^1$ to N, each optionally substituted by lower alkyl, or by an unsubstituted Ar or Ar$^1$ group as defined above; and B is an alkylene group of 3 or 4 carbon atoms which may be substituted by lower alkyl, wherein lower in connection with alkyl refers to such groups having 1 to 6 carbon atoms providing that neither Ar—A of Ar$^1$—A$^1$ is benzyl or phenethyl, substituted with one or more lower alkyl groups.

2. A compound according to claim 1 wherein B is —(CH$_2$)$_3$— or —(CH$_2$)$_4$— or such a group substituted by methyl.

3. A compound according to claim 1 wherein R$^1$ and/or R$^2$ are/is hydrogen, methyl, ethyl, propyl or benzyl.

4. A compound according to claim 1 in which the compound of formula Ia is 4-[N,N-bis-(4-chlorobenzyl)-amino]butyric acid or a pharmaceutically acceptable salt thereof.

5. A compound according to claim 1 in which the compound of formula Ia is 4-[N,N-bis-(3,4-dichlorobenzyl)amino]butyric acid or a pharmaceutically acceptable salt thereof.

6. A compound according to claim 1 in which the compound of formula Ia is 4-[N,N-bis-(3,4-methoxybenzyl) amino]butyric acid or a pharmaceutically acceptable salt thereof.

7. A compound according to claim 1 in which the compound of formula Ia is 4-(N,N-bis-[2-(4-chlorophenyl)ethyl]amino) butyric acid or a pharmaceutically acceptable salt thereof.

8. A compound according to claim 1 in which the compound of formula Ia is 4-[(N-(1,1-diphenyl)methyl-N-benzyl)amino]butyric acid or a pharmaceutically acceptable salt thereof.

9. A compound according to claim 1 in which the compound of formula Ia is 4-[N,N-bis-(3-bromobenzyl)amino]butanoic acid or a pharmaceutically acceptable salt thereof.

10. A compound according to claim 1 in which the compound of formula Ia is 4-[N,N-bis-(3-chlorobenzyl)amino]butanoic acid or a pharmaceutically acceptable salt thereof.

11. A compound according to claim 1 in which the compound of formula Ia is 4-[(N-4-methylphenylmethyl-N-phenylmethyl)amino]-butanoic acid or a pharmaceutically acceptable salt thereof.

12. A compound according to claim 1 in which the compound of formula Ia is 4-[N,N-bis-(1-naphthalenemethyl)amino]butanoic acid or a pharmaceutically acceptable salt thereof.

13. A compound according to claim 1 wherein Ar and Ar$^1$ are independently selected from optionally substituted phenyl or naphthyl.

14. A compound according to claim 1 wherein A and A$^1$ are independently selected from —CHR$^3$, where R$^3$ is hydrogen, lower alkyl or an optionally substituted Ar group.

15. A compound of formula Ib

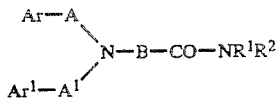

or a pharmaceutically acceptable salt thereof, wherein

Ar and Ar$^1$ are the same or different mono- or bicyclic carbocyclic aryl groups of 6 to 10 carbon atoms, optionally substituted by one or more substituents selected from lower alkyl, lower alkoxy, halogen, haloloweralkyl, haloloweralkoxy, cyano, amino, loweralkylamino, di-loweralkylamino and nitro;

A and A$^1$ are the same of different alkylene groups having one or two carbon atoms linking Ar and Ar$^1$ to N, each optionally substituted by lower alkyl, or by an unsubstituted Ar or Ar$^1$ group as defined above;

B is an alkylene group of 3 or 4 carbon atoms which may be substituted by lower alkyl; and R$^1$ and R$^2$ are independently hydrogen lower alkyl or aralkyl of 7 to 12 carbon atoms, wherein lower in connection with alkyl refers to such groups having 1 to 6 carbon atoms, providing that neither Ar-A or Ar$^1$-A$^1$ substituted or unsubstituted benzyl.

16. A compound according to claim 15 wherein Ar and Ar$^1$ are independently selected from optionally substituted phenyl or naphthyl.

17. A compound according to claim 15 wherein A and A$^1$ are independently selected from —CHR$^3$, wherein R$^3$ is hydrogen, lower alkyl or an optionally substituted Ar group.

18. A compound according to claim 15 wherein B is —(CH$_2$)$_3$—or —(CH$_2$)$_4$— or such a group substituted by methyl.

19. A compound according to claim 15 wherein R$^1$ and/or R$^2$ are/is hydrogen, methyl, ethyl, propyl or benzyl.

20. A pharmaceutical composition comprising a compound of formula Ia

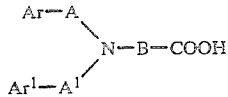

or a pharmaceutically acceptable salt thereof, wherein

Ar and Ar$^1$ are the same or different mono- or bicyclic carbocyclic aryl groups of 6 to 10 carbon atoms, Ar and Ar$^1$ being each, independently, optionally substituted by one or more substiuents selected from lower alkyl, lower alkoxy, halogen, haloloweralkyl, haloloweralkoxy, cyano, amino, loweralkylamino, di-loweralkylamino, and nitro;

A and A$^1$ are the same of different alkylene groups having one or two carbon atoms linking Ar or Ar$^1$ to N, each optionally substituted by lower alkyl, or by an unsubstituted Ar or Ar$^1$ group as defined above; and B is an alkylene group of 3 or 4 carbon atoms which may be substituted by lower alkyl, wherein lower in connection with alkyl refers to such groups having 1 to 6 carbon atoms, and a pharmaceutically acceptable carrier.

21. A pharmaceutical composition comprising a compound according to claim 15 or a pharmaceutically acceptable salt thereof and a pharmaceutically acceptable carrier.

* * * * *